US012331282B2

(12) United States Patent
Wang et al.

(10) Patent No.: US 12,331,282 B2
(45) Date of Patent: Jun. 17, 2025

(54) STRAIN FOR PRODUCING LONG-CHAIN DICARBOXYLIC ACIDS AND FERMENTATION METHOD THEREFOR

(71) Applicants: CATHAY BIOTECH INC., Shanghai (CN); CIBT AMERICA INC., Newark, DE (US)

(72) Inventors: Jianglin Wang, Shanghai (CN); Wei Li, Shanghai (CN); Qinpei Li, Shanghai (CN); Wenxiao Jiang, Shanghai (CN); Shuya Min, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 531 days.

(21) Appl. No.: 17/769,459

(22) PCT Filed: Jan. 16, 2020

(86) PCT No.: PCT/CN2020/072398
§ 371 (c)(1),
(2) Date: Apr. 15, 2022

(87) PCT Pub. No.: WO2021/073011
PCT Pub. Date: Apr. 22, 2021

(65) Prior Publication Data
US 2023/0203431 A1 Jun. 29, 2023

(30) Foreign Application Priority Data
Oct. 18, 2019 (CN) .......................... 201910992388.0

(51) Int. Cl.
*C12N 1/16* (2006.01)
*C12P 7/44* (2006.01)
*C12R 1/74* (2006.01)

(52) U.S. Cl.
CPC ............... *C12N 1/165* (2021.05); *C12P 7/44* (2013.01); *C12R 2001/74* (2021.05)

(58) Field of Classification Search
CPC ... C12N 1/165; C12N 1/16; C12P 7/44; C12P 7/6409; C12R 2001/74
See application file for complete search history.

(56) References Cited

U.S. PATENT DOCUMENTS

| 10,851,394 B2 | 12/2020 | Xu et al. |
| 2019/0271012 A1 | 9/2019 | Xu et al. |

FOREIGN PATENT DOCUMENTS

| CN | 102839133 A | 12/2012 |
| CN | 107326051 A | 11/2017 |
| CN | 109913512 A | 6/2019 |
| CN | 109943598 A | 6/2019 |
| CN | 109943599 A | 6/2019 |
| CN | 110218661 A | 9/2019 |
| CN | 110218745 A | 9/2019 |
| CN | 110218746 A | 9/2019 |
| KR | 20170048763 A | 5/2017 |

OTHER PUBLICATIONS

Songnaka, N. et al. Atmospheric and Room Temperature Plasma (ARTP) Mutagenesis Improved the Anti-MRSA Activity of *Brevibacillus* sp. SPR20, 2023, International Journal of Molecular Sciences, 24(15): 1-20 (Year: 2023).*

Kalahroudi, R. et al. Increment in protease activity of Lysobacter enzymogenes strain by ultra violet radiation, 2020, Iranian Journal of Microbiology, 12(6): 601-606 (Year: 2020).*

International Search Report and the Written Opinion of the International Searching Authority, issued in corresponding International Application No. PCT/CN2020/072398, dated Jul. 15, 2020, 3 pages.

* cited by examiner

*Primary Examiner* — Louise W Humphrey
*Assistant Examiner* — Anjali Ajit Hirani
(74) *Attorney, Agent, or Firm* — Rothwell, Figg, Ernst & Manbeck, P.C.

(57) ABSTRACT

Provided are a *Candida tropicalis* strain Am2525, with the preservation number thereof being CCTCC NO: M 2019419, and a method for producing long-chain dicarboxylic acids by means of fermenting the strain. The method for producing the long-chain dicarboxylic acids comprises preparing a seed solution by means of the *Candida tropicalis* strain Am2525 and producing the long-chain dicarboxylic acids via fermentation of the seed solution. Compared with the parent, the *Candida tropicalis* strain Am2525 has an enhanced resistance to the toxicity of a substrate decane, improves the productivity of long-chain dicarboxylic acids, reduces the cost of production, subsequent separation and purification are simple, and the fermentation production process is easy to implement on a large scale.

12 Claims, 2 Drawing Sheets

STRAIN FOR PRODUCING LONG-CHAIN DICARBOXYLIC ACIDS AND FERMENTATION METHOD THEREFOR

CROSS REFERENCE TO RELATED APPLICATION(S)

This application is a 35 U.S.C. § 371 National Phase Entry Application from PCT/CN2020/072398, filed Jan. 16, 2020, designating the United States, and also claims the benefit of Chinese Application No. 201910992388.0, filed Oct. 18, 2019, the disclosures of which are incorporated herein by reference in their entirety.

TECHNICAL FIELD

The present invention belongs to the field of biotechnology, in particular to a strain, especially to a strain for producing a long-chain dicarboxylic acid, and a method for producing a long-chain dicarboxylic acid via fermentation by using the strain.

BACKGROUND ART

Long-chain dicarboxylic acids are important raw materials for synthesizing perfumes, engineering nylon plastics, hot melt adhesives, resins, cold resistant plasticizers, medicines, pesticides and the like, and have a structural formula of $HOOC(CH_2)_nCOOH$, wherein n is an integer greater than 7. Among them, decanedioic acid, also known as 10-C long-chain decanedioic acid and sebacic acid, has a chemical formula of $HOOC(CH_2)_8COOH$. As an important monomeric raw material, it has been widely used in the production of engineering polyamide plastics such as nylon 510, nylon 1010, and nylon 610. As one of the widely used chemical raw materials, it can also be used in high temperature resistant lubricating oil, epoxy resin curing agents, synthetic lubricating grease, synthetic perfumes, cold resistant plasticizers and the like.

At present, industrially produced and applied decanedioic acid is chemically prepared by using castor oil as raw material. The process mainly includes the steps of hydrolyzing castor oil into sodium ricinoleate from which ricinoleic acid is prepared, pyrolyzing ricinoleic acid by adding a base and by heating in the presence of phenol to generate decanedioic acid disodium salt, then further heating, adding an acid, decolorizing and crystallizing to obtain decanedioic acid. The preparation process of producing decanedioic acid by catalytically pyrolyzing castor oil is complicated, involving reacting at a high temperature of 250° C. to 270° C. and using a toxic reagent such as phenol or o-cresol, resulting in pollution to the environment, which seriously limit the development of the industry of chemically producing decanedioic acid.

The biological process of preparing decanedioic acid is characterized by simple process, going green and environmental protection. Yu Zhihua from the Institute of Microbiology, Chinese Academy of Sciences (see Acta Microbiologica Sinica, 1989 Issue 06: 0253-2654) obtained a high-producing strain by mutation screening, and achieved a yield of up to 71 g/L of decanedioic acid in a 16 L fermentation tank, and obtained a decanedioic acid product by aqueous phase crystallization with a purity of above 99.6%. The production of decanedioic acid by fermenting the *Candida lipolytica* screened by the Institute of Forest Soil Science, Chinese Academy of Sciences (see Acta Microbiologica Sinica, 1979 Issue 01) achieved a yield of 30-40 g/L of.

During the preparation of decanedioic acid by a biological process, decane or an analogue thereof is usually used as the substrate for fermentation. Such kind of substrates, during the possible transformation pathways in the fermentation, are oxidized in multiple steps by thalli to the target product decanedioic acid, consumed by thalli for growth maintenance or violated into external environment, etc. However, decane, due to its own properties, may have toxic effects on microorganisms and inhibit the growth of microorganisms in the fermentation process. Therefore, an important research aim is to modify a strain so as to enhance the toxin-resistant ability of the strain.

SUMMARY OF THE INVENTION

In the first aspect, the present disclosure aims to provide a *Candida tropicalis* strain to solve the problems in the production of decanedioic acid from *Candida tropicalis* strains at present such as low thallus concentration, long fermentation period and low conversion efficiency, and thus solve the technical problem of high production cost.

The present disclosure solves the above problems by the following technical solution to achieve the objective of the first aspect of the present disclosure.

The present disclosure provides a *Candida tropicalis* strain, *Candida tropicalis* Am2525 with a deposition number CCTCC NO: M 2019419.

The strain provided in the present disclosure is *Candida tropicalis* Am2525, which is screened out by using the strain *Candida tropicalis* CAT N145 of producing mixed dicarboxylic acids through oxidizing n-alkanes (which was deposited on Jun. 9, 2011 under accession number CCTCC M 2011192 in the China Center for Type Culture Collection (CCTCC) in Wuhan University) as a starting strain and performing compound mutation of atmospheric and room temperature plasma (ARTP) and ultraviolet irradiation.

The *Candida tropicalis* Am2525 has the following morphological characteristics: its colony has a smooth and wet surface which is milk-white, glossy, rounded, and neat in edge.

In the second aspect, the present disclosure aims to provide use of the aforementioned *Candida tropicalis* strain Am2525 in producing a long-chain dicarboxylic acid.

The present disclosure provides use of the aforementioned *Candida tropicalis* strain Am2525 in producing decanedioic acid.

In a preferred embodiment, the substrate for fermentation conversion in the production of decanedioic acid is one or more selected from the group consisting of C10 n-alkanes, C10 straight-chain saturated fatty acids, C10 straight-chain saturated fatty acid esters and C10 straight-chain saturated fatty acid salts.

In the third aspect, the present disclosure aims to provide a method of producing a long-chain dicarboxylic acid, in particular, a method of producing decanedioic acid, to solve the problems during the production of decanedioic acid from a *Candida tropicalis* strain at present such as low thallus concentration, long fermentation period and low conversion efficiency, and thus solve the technical problem of high production cost.

The present disclosure solves the above problems by the following technical solution to achieve the objective of the third aspect of the present disclosure.

A method of producing a long-chain dicarboxylic acid, comprising preparing a seed solution from *Candida tropicalis* strain Am2525, and/or producing a long-chain dicarboxylic acid by fermentation.

Further, the long-chain dicarboxylic acid is preferably a C10 straight-chain saturated dicarboxylic acid.

In a preferred embodiment, the substrate for fermentation includes one or more selected from the group consisting of C10 n-alkanes, C10 straight-chain saturated fatty acids, C10 straight-chain saturated fatty acid esters and C10 straight-chain saturated fatty acid salts. Preferably, the substrate for fermentation is added in an amount of 100-400 mL/L, wherein the volume ratio is the volume ratio of the substrate to fermentation medium.

In a preferred embodiment, the seed solution is prepared at a temperature of 27° C. to 31° C.; decanedioic acid is produced by fermentation at a fermentation temperature in a range of 27° C. to 31° C.

The selection of medium is important for strain fermentation. Based on any technical solution described above, in the method of producing a long-chain dicarboxylic acid, the fermentation medium for fermentation comprises:
carbon source 10 g/L to 40 g/L;
nitrogen sources each being at a concentration of 0.5-10 g/L; and
inorganic salts each being at a concentration of 0.5-12 g/L.

Further, the carbon source comprises one or more selected from the group consisting of sucrose, glucose, maltose, molasses, fructose, rhamnose, arabinose and sorbitol.

The nitrogen sources comprise one or more selected from the group consisting of yeast extract, corn steep liquor, urea, ammonium hydroxide, ammonium sulfate, potassium nitrate and ammonium nitrate.

The inorganic salts comprise one or more selected from the group consisting of a potassium salt and a sodium salt; preferably, the potassium salt comprises one or more selected from the group consisting of potassium chloride, potassium nitrate, potassium dihydrogen phosphate and dipotassium hydrogen phosphate, and the sodium salt comprises one or more selected from the group consisting of sodium chloride, sodium nitrate, sodium dihydrogen phosphate and disodium hydrogen phosphate.

Preferably, the fermentation medium comprises:
Sucrose 10-40 g/L
corn steep liquor 1-5 g/L
yeast extract 1-5 g/L
potassium dihydrogen phosphate 4-12 g/L
potassium nitrate 4-10 g/L
sodium chloride 0-3 g/L
urea 0.5-3 g/L.

Based on any technical solution described above, the method of producing a long-chain dicarboxylic acid further comprises the following steps:
a) activating the strain;
b) preparing a seed solution using a seed culture medium; and
c) inoculating the seed solution into a fermentation medium for fermentation.

Still further, in step a), the medium for activating the strain comprises YPD medium. The YPD medium comprises 2.0% (w/v) of glucose, 1.0% (w/v) of yeast extract, 2.0% (w/v) of peptone, and water for balance.

Still further, in step b), the seed culture medium comprises: 10-20 g/L of sucrose, 2-4 g/L of corn steep liquor, 3-8 g/L of yeast extract, 4-12 g/L of potassium dihydrogen phosphate, 0.5-4 g/L of urea, and 0-80 mL/L of one or more selected from the group consisting of C10 n-alkanes, C10 straight-chain saturated fatty acids, C10 straight-chain saturated fatty acid esters and C10 straight-chain saturated fatty acid salts.

Preferably, in step b), the culture time for preparing the seed solution is 12-48 hours, and the indicator of seed maturation is that OD620 after 30-fold dilution with water is from 0.5 to 1.0.

Preferably, in step c), when inoculating the seed solution into the fermentation medium for fermentation, the seed solution is inoculated into the medium in an inoculation amount of 10%-30% by volume.

Preferably, in step c), the fermentation comprises culturing at 28° C. to 31° C. and at a shaking speed of 200-250 rpm. A fermentation cycle starts from the inoculation of the substrate and ends up with no obvious substrate residue in fermentation broth, and the fermentation cycle of the strain in a fermentation system is 90-200 hours.

The strain has the conversion efficiency of the substrate of above 35%, further preferably above 40% in a fermentation system.

Compared with prior art, the present disclosure has the following significant characteristics and positive effects:

Compared with the parent strain, the *Candida tropicalis* strain of the present disclosure has enhanced resistance to the toxicity of the substrate decane, so that a higher OD of thalli can be achieved in both growth and fermentation processes, converting more substrate, increasing production capacity, lowering production cost and simplifying subsequent separation and purification. The fermentation production process is easy to scale up and has good application prospects.

INFORMATION OF DEPOSIT

Strain: *Candida tropicalis* Am2525
Deposition date: Jun. 3, 2019
Deposition institute: China Center for Type Culture Collection (Address: Wuhan University, Wuhan, China)
Deposition number: CCTCC NO: M 2019419

DETAILED DESCRIPTION OF THE INVENTION

Figure 1:
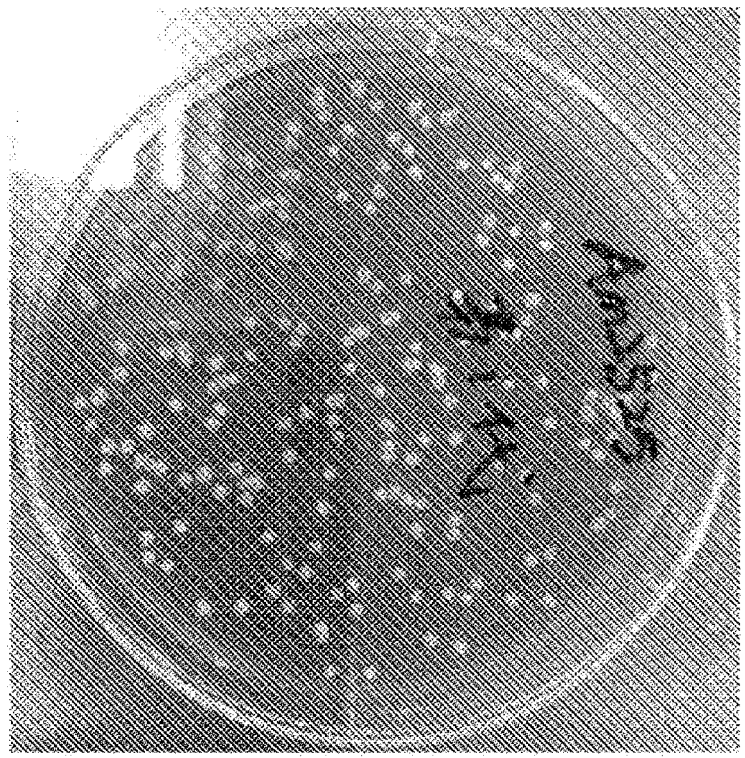
FIG. 1 is an image of the first generation colonies of *Candida tropicalis* Am2525 of the present disclosure.

The present disclosure is described in detail in combination with the accompanying drawings.

By using the long-chain dicarboxylic acid-producing strain *Candida tropicalis* CAT N145 (this strain was disclosed in the Chinese invention patent No. CN 102839133A published on Dec. 26, 2012; in that patent procedure, it was deposited in the China Center for Type Culture Collection (CCTCC) in Wuhan University on Jun. 9, 2011 under deposition number CCTCC M 2011192) as starting strain, through mutation breeding by means of acclimation and routine mutagenesis methods, e.g. with reference to the method disclosed in the Chinese patent No. CN201110138270.5, the inventors of the present application screened out a new strain of *Candida tropicalis*, designated as *Candida tropicalis* Am2525 which could efficiently convert C10 n-alkanes, C10 straight-chain saturated fatty acids, C10 straight-chain saturated fatty acid derivatives (such as straight-chain saturated fatty acid esters, straight-chain saturated fatty acid salts) or a mixture of more than two of them to decanedioic acid.

A method of producing decanedioic acid comprises the following steps:
  a) activating a strain: in a preferred particular embodiment, activating a strain is carried out by culturing on a shaker for 1-2 days; the medium for activating a strain comprises YPD medium, preferably the YPD medium comprises 2.0% (w/v) of glucose, 1.0% (w/v) of yeast extract, 2.0% (w/v) of peptone and water for balance.
  b) preparing a seed solution by using a seed culture medium: in a preferred particular embodiment, preparing a seed solution by using a seed culture medium is carried out by culturing at 27° C. to 31° C., preferably 29° C., for 24-48 hours; when the $OD_{620}$ of the seed solution is 0.5-1.0 (after 30-fold dilution with water), the seed solution is inoculated into a shake flask containing a fermentation medium. The seed culture medium comprises 10-20 g/L of sucrose, 2-4 g/L of corn steep liquor, 3-8 g/L of yeast extract, 4-12 g/L of potassium dihydrogen phosphate, 0.5-4 g/L of urea and 0-80 mL/L of one or more selected from the group consisting of C10 n-alkanes, C10 straight-chain saturated fatty acids and C10 straight-chain saturated fatty acid derivatives (such as straight-chain saturated fatty acid esters and straight-chain saturated fatty acid salts).
  c) inoculating the seed solution into a fermentation medium for fermentation, and decanedioic acid is produced by fermenting the *Candida tropicalis* strain Am2525 as described above.

In step c), the fermentation is carried out preferably at a temperature in a range of 27° C. to 31° C., more preferably 29° C.

The substrate for fermentation comprises one or more selected from the group consisting of C10 n-alkanes, C10 straight-chain saturated fatty acids, C10 straight-chain saturated fatty acid esters and C10 straight-chain saturated fatty acid salts; preferably, the substrate for fermentation is added in an amount of 100-400 mL/L, wherein the volume ratio is the volume ratio of the substrate to the fermentation medium.

The fermentation medium comprises:
  carbon source 10 g/L to 40 g/L;
  nitrogen sources each being at a concentration of 0.5-10 g/L
  inorganic salts each being at a concentration of 0.5-12 g/L.

The carbon source comprises one or more selected from the group consisting of sucrose, glucose, maltose, molasses, fructose, rhamnose, arabinose and sorbitol.

The nitrogen sources comprise one or more selected from the group consisting of yeast extract, corn steep liquor, urea, ammonium hydroxide, ammonium sulfate, potassium nitrate and ammonium nitrate.

The inorganic salts comprise one or more selected from the group consisting of a potassium salt and a sodium salt; preferably, the potassium salt comprises one or more selected from the group consisting of potassium chloride, potassium nitrate, potassium dihydrogen phosphate and dipotassium hydrogen phosphate, and the sodium salt comprises one or more selected from the group consisting of sodium chloride, sodium nitrate, sodium dihydrogen phosphate and disodium hydrogen phosphate.

In one preferred example, the fermentation medium comprises:
  sucrose 10-40 g/L
  corn steep liquor 1-5 g/L
  yeast extract 1-5 g/L
  potassium dihydrogen phosphate 4-12 g/L
  potassium nitrate 4-10 g/L
  sodium chloride 0-3 g/L
  urea 0.5-3 g/L.

At the beginning of fermentation, the concentration of the substrate in the fermentation broth is 100-400 mL/L, and the pH of the medium is adjusted to 7.5 with NaOH solution.

In the present disclosure, a substrate added to the medium is one or more selected from the group consisting of n-alkanes, straight-chain saturated fatty acids and straight-chain saturated fatty acid derivatives; preferably, the substrate comprises one or more selected from the group consisting of C10 n-alkanes, C10 straight-chain saturated fatty acids, C10 straight-chain saturated fatty acid esters and C10 straight-chain saturated fatty acid salts.

The method for measuring dicarboxylic acids used in the examples is as follows:

Detection of the dicarboxylic acid content in a fermentation broth: gas chromatographic detection (internal standard method) after pre-treatment of fermentation broth under the chromatography conditions: column: Supelco SPB-50 30 m*0.53 mm*0.5 μm (Cat No: 54983). Gas chromatograph (Shimadzu, GC-2014).

Method: initial temperature 100° C., increasing to 230° C. at a rate of 15° C./min, and then keeping for 2 minutes. Hydrogen is used as carrier gas; a sample inlet temperature is 280° C., the FID temperature is 280° C., and a sample loading volume is 4 μL.

The concentration of the product is calculated as a function of the ratio of the area of the product peak to an internal standard peak area with a known concentration.

A method for measuring a residual alkane content in the following examples is as follows:
Measured by a Centrifugation Process:
  (1) taking 6 mL of dicarboxylic acid fermentation broth (the volume of the fermentation broth is $V_{total}$), and adding 3 mL of 0.1 mol/L sodium hydroxide solution to the fermentation broth, and then heating in a water bath kettle at 80° C. for 10 minutes.
  (2) cooling, centrifugation at 3000 r/min for 10 minutes, and reading after centrifugation the volume of the oil layer $V_{oil}$ and the volume of the emulsion layer $V_{emulsion}$.

Note: the centrifugal tube shall be scaled.

(For example, $V_{oil}/V_{emulsion}/V_{total}$=0.1:0.2:6, where $V_{oil}$ 0.1 refers to the height of the oil layer in the scaled tube; $V_{emulsion}$ 0.2 refers to the height of the emulsion layer in the scaled tube; and $V_{total}$ 6 refers to the volume 6 mL of the dicarboxylic acid fermentation broth).

YPD medium comprises 2.0% (w/v) of glucose, 1.0% (w/v) of yeast extract, 2.0% (w/v) of peptone and water for balance.

Example 1

Figure 2:
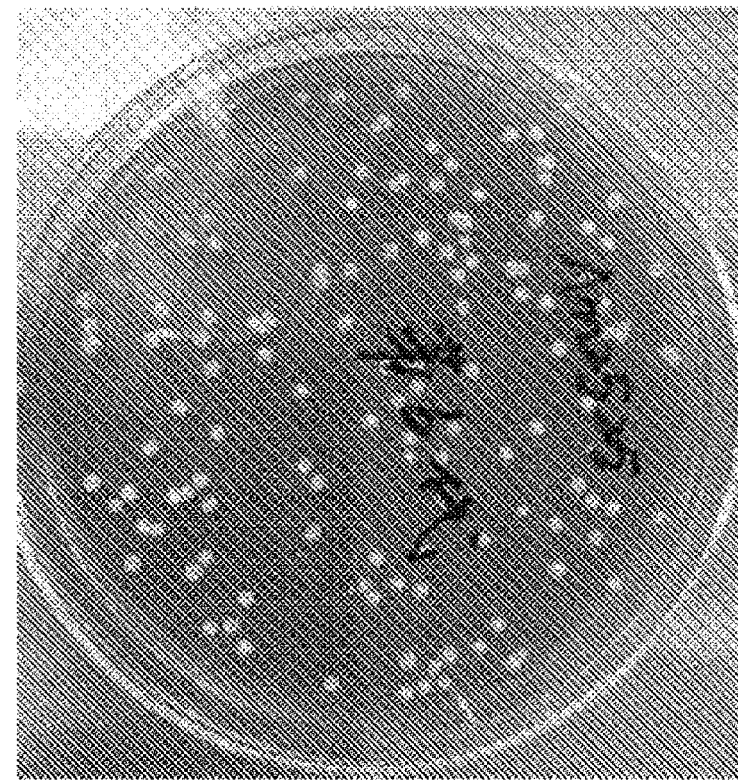
FIG. 2 is an image of the sixth generation colonies of *Candida tropicalis* Am2525 of the present disclosure.
Figure 3:
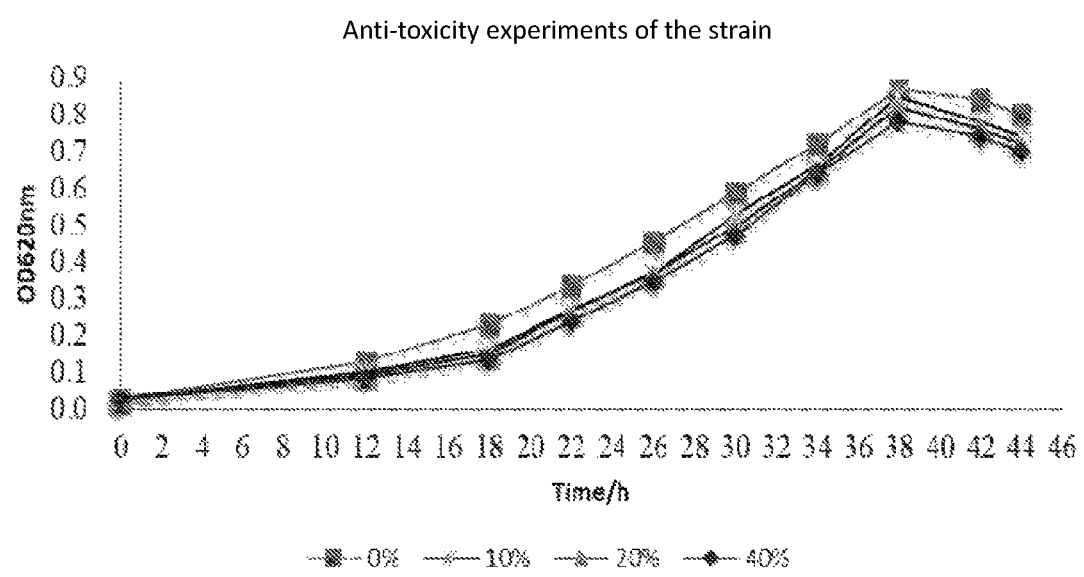
FIG. 3 is growth curves of *Candida tropicalis* Am2525 in seed culture media containing decane at starting concentrations of 10%, 20% and 40% (v/v).

Verified by passage experiment, *Candida tropicalis* Am2525 of the present disclosure exhibited no obvious change in both colonial morphology and decanedioic acid production capacity after five passages (see FIG. 1 and FIG. 2). At 29° C., the first and sixth generation strains produced 140.5 g/L and 139.8 g/L of DC10 by shaking fermentation, respectively (adding 4.5 mL of nC10 as the substrate). Colonial morphology: each colony had a smooth and wet surface which was milk-white, glossy, rounded, and neat in edge. It thus could be seen that the *Candida tropicalis*

Am2525 of the present disclosure had good passage stability. When the concentration of decane was in a range of 0 to 100 mL/L, the *Candida tropicalis* strain Am2525 exhibited complete and smooth surface, indicating that the cellular morphology of the strain had robust tolerance to decane.

To further verify the tolerance of the thalli in decane at a higher concentration, the growth status of the thalli was assayed under volume ratios of decane to seed culture medium of 10%, 20% and 40%, respectively, with a seed culture medium without decane as blank control, and each experiment was done in triplicate.

Experimental results showed that at the decane concentrations of 10%, 20% and 40% (v/v), the growth of the *Candida tropicalis* Am2525 was inhibited at the beginning but rapidly increased later, and was close to that of the control in 48 hours.

Example 2

One seed preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 ml/L of nC10. After culturing at 29° C. for 48 hours, the OD620 of the seed solution reached 0.7 (after 30-fold dilution with water). 3.0 ml of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 4.5 mL of n-alkane nC10 was added to the fermentation medium, and the fermentation medium was sterilized at 121° C. for 20 minutes. Fermentation was carried out at 29° C., and was stopped when the fermentation substrate in the fermentation broth was assayed to be 0, and the period was 160 hours.

After the completion of fermentation, it was measured that the content of DC10 dicarboxylic acid in the fermentation broth was 140 g/L, an average acid production rate was 0.88 g/h·L, and the mass conversion rate of the substrate was 63.94%.

Example 3

One seed preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, and 2 g/L of urea. After culturing at 29° C. for 48 hours, the OD620 of the seed solution reached 0.8 (after 30-fold dilution with water). 3.0 ml of the seed solution was inoculated into a shake flask containing a fermentation medium (15 ml of the fermentation medium was used), where the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 4.5 ml of n-alkane nC10 was added to the fermentation medium, and the fermentation medium was sterilized at 121° C. for 20 minutes. The fermentation was carried out at 29° C., and stopped when the fermentation substrate in the fermentation broth was assayed to be 0, and the period was 180 hours.

After the completion of the fermentation, it was measured that the content of DC10 dicarboxylic acid in the fermentation liquor was 120 g/L, an average acid production rate was 0.67 g/h·L, and the mass conversion rate of the substrate was 54.8%.

Example 4

One seed preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 mL/L of nC10. After culturing at 29° C. for 48 hours, the OD620 of the seed solution reached 0.7 (after 30-fold dilution with water). 3.0 ml of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 1.5 ml of n-alkane nC10 was added to the fermentation medium, and the fermentation medium was sterilized at 121° C. for 20 minutes. The fermentation was carried out at 29° C., and stopped when the fermentation substrate in the fermentation broth was assayed to be 0, and the period was 124 hours.

After the completion of the fermentation, it was measured that the content of DC10 dicarboxylic acid in the fermentation broth was 46 g/L, an average acid production rate was 0.37 g/h·L, and the mass conversion rate of the substrate was 63.1%.

Example 5

One seed preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 ml/L of nC10. After culturing at 29° C. for 48 hours, the OD620 of the seed solution reached 0.7 (after 30-fold dilution with water). 3.0 mL of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 6.0 ml of n-alkane nC10 was added to the fermentation medium, and the fermentation medium was sterilized at 121° C. for 20 minutes. The fermentation was carried out at 29° C., and stopped when the fermentation substrate in the fermentation broth was assayed to be 0, and the period was 192 hours.

After the completion of the fermentation, it was measured that the content of DC10 dicarboxylic acid in the fermentation broth was 194 g/L, an average acid production rate was 1.01 g/h·L, and the mass conversion rate of the substrate was 66.46%.

Example 6

One seed preserved in a glycerin tube was inoculated into a seed culture medium and cultured at 28° C. When the optical density (OD620) of the thalli in the seed solution reached 0.5 (after 30-fold dilution with water), the seed solution was inoculated into a fermentation medium in an inoculation amount of 10% (v/v) for fermentable conversion. The fermentation temperature was controlled to be 30° C., and during the fermentation, the pH was 7.2, aeration volume was controlled to be 0.3 vvm, and the pressure in the fermenter was controlled to be 0.08 MPa. A certain stirring speed was kept, and the dissolved oxygen during the fermentation was maintained at above 20%. After the seed solution was inoculated into the fermenter, thalli started to grow and propagate, and when the optical density (OD620) of the thalli in the fermentation broth reached 0.5 (after 30-fold dilution with water), a fermentation substrate n-decane was added. The feeding rate of decane was controlled by feeding technique so that the concentration of decane in the fermentation broth during the fermentation was in a range of 4% to 6% (v/v), and the total amount of the fermentation substrate decane added was 1300 g. The fermentation was stopped when the fermentation substrate in the fermentation broth was assayed to be 0, and the fermentation time was 140 hours.

Detection results: after the completion of the fermentation, the yield of C10 dicarboxylic acid in the fermentation broth was 195 g/L, the conversion rate of the substrate was 90%, and an average acid production rate was 1.39 g/h·L.

Example 7

One seed preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 mL of C10 fatty acid methyl ester. After culturing at 29° C. for 48 hours, the OD620 of the seed solution reached 0.7 (after 30-fold dilution with water). 3.0 ml of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 4.5 mL of C10 fatty acid methyl ester was added to the fermentation medium, and the fermentation medium was sterilized at 121° C. for 20 minutes. The fermentation was carried out at 29° C., and stopped when the fermentation substrate in the fermentation broth was assayed to be 0, and the period was 162 hours.

After the completion of the fermentation, it was measured that the content of DC10 dicarboxylic acid in the fermentation broth was 125 g/L, an average acid production rate was 0.77 g/h·L, and the mass conversion rate of the substrate was 47.66%.

Comparative Example 1

One tube of *Candida tropicalis* CAT N145 preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 mL/L of nC10. After culturing at 29° C. for 48 hours, the OD620 of the seed solution reached 0.55 (after 30-fold dilution with water). 3.0 mL of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 1.5 mL of n-alkane nC10 was added to the fermentation medium, and the fermentation medium was sterilized at 121° C. for 20 minutes. The fermentation was carried out at 29° C., and stopped when the fermentation substrate in the fermentation broth was assayed to be 0, and the fermentation period was 140 hours.

After the completion of the fermentation, it was measured that the content of DC10 dicarboxylic acid in the fermentation broth was 30 g/L, an average acid production rate was 0.21 g/h·L, and the mass conversion rate of the substrate was 41.11%.

Comparative Example 2

One tube of *Candida tropicalis* CAT N145 preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 mL/L of nC10. After culturing at 29° C. for 48 hours, the OD620 of the seed solution reached 0.55 (after 30-fold dilution with water). 3.0 ml of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 6.0 mL of n-alkane nC10 was added to the fermentation medium, and the fermentation medium was sterilized at 121° C. for 20 minutes. The fermentation was carried out at 29° C., and the fermentation period was 230 hours. The fermentation was stopped when the consumption rate of the substrate was significantly reduced (sampling at an interval of 10 hours from 200 hours to detect the substrate content).

After the completion of the fermentation, it was measured that the content of DC10 dicarboxylic acid in the fermentation broth was 116.8 g/L, an average acid production rate was 0.51 g/h·L, and the mass conversion rate of the substrate was 40%.

Comparative Example 3

One tube of *Candida tropicalis* CAT N145 preserved in a glycerin tube was inoculated into YPD activation medium, and after culturing for 24 hours, a culture solution was inoculated into a seed culture medium (which was sterilized at 121° C. for 20 minutes). The seed culture medium comprises: 20 g/L of sucrose, 2 g/L of corn steep liquor, 6 g/L of yeast extract, 8 g/L of potassium dihydrogen phosphate, 2 g/L of urea, and 1 mL/L of nC10. After culturing at 29° C. for 48 hours, the OD620 of the seed solution reached 0.55 (after 30-fold dilution with water). 3.0 ml of the seed solution was inoculated into a shake flask containing a fermentation medium (15 ml of the fermentation medium was used), wherein the fermentation medium comprises: 30 g/L of sucrose, 5 g/L of corn steep liquor, 5 g/L of yeast extract, 8 g/L of potassium dihydrogen phosphate, 4 g/L of potassium nitrate, 1.5 g/L of sodium chloride, and 0.5 g/L of urea. 4.5 mL of n-alkane nC10 was added to the fermentation medium, and the fermentation medium was sterilized at 121° C. for 20 minutes. The fermentation was carried out at 29° C., and the fermentation period was 180 hours. The fermentation was stopped when the consumption rate of the substrate was significantly reduced (sampling at an interval of 10 hours from 150 hours for detecting the substrate content).

After the completion of the fermentation, it was measured that the content of DC10 dicarboxylic acid in the fermentation broth was 108 g/L, an average acid production rate was 0.6 g/h·L, and the mass conversion rate of the substrate was 49.33%.

Comparative Example 4

The *Candida tropicalis* CATN145 thalli were inoculated into a seed culture medium and cultured at 28° C. When the optical density (OD620) of the thalli in the seed solution reached 0.5 (after 30-fold dilution with water), the seed solution was inoculated into a fermentation medium in an inoculation amount of 10% (v/v) for fermentable conversion. The fermentation temperature was controlled to be 30° C., and during the fermentation, the pH was 7.2, the aeration volume was 0.3 vvm, and the pressure in the fermenter was controlled to be 0.08 MPa. A certain stirring speed was kept, and the dissolved oxygen during the fermentation was maintained at above 20%. After the seed solution was inoculated into the fermenter, the thalli started to grow and propagate, and when the optical density (OD620) of the thalli in the fermentation broth reached 0.5 (after 30-fold dilution), a fermentation substrate n-decane was added. The feeding rate of decane was controlled by feeding technique so that the concentration of decane in the fermentation broth during the fermentation was in a range of 4% to 6% (v/v), and the total amount of the fermentation substrate decane added was 1300 g. The fermentation time was 160 hours. The fermentation was stopped when the consumption rate of the substrate was significantly reduced (sampling at an interval of 10 hours from 150 hours for detecting the substrate content).

After the completion of the fermentation, the yield of C10 dicarboxylic acid in the fermentation broth was 144 g/L, the mass conversion rate of the substrate was 66.4%, and the average acid production rate was 0.9 g/h·L.

As could be seen from the above examples, the *Candida tropicalis* strain Am2525 used in the present disclosure had better resistance to the substrate decane than the parent *Candida tropicalis* CATN145 thalli. When the feeding substrate decane exceeded 4%-6% (v/v), the mass conversion rate of the *Candida tropicalis* strain Am2525 on the substrate was maintained at above 90%, and the average acid production rate reached 1.39 g/h·L. Therefore, the *Candida tropicalis* strain Am2525 of the present disclosure can be useful in the enzymatically industrial production of C10 dicarboxylic acid.

Finally, it should be noted that the above examples are merely intended to illustrate the technical solutions of the present disclosure, but not limitative. Although the present disclosure is described in detail with reference to the above examples, those of ordinary skill in the art will understand that modifications can be made to the technical solutions described in the above examples or equivalent replacements to some or all technical features thereof can be made, and such modifications or replacements do not make the essence of corresponding technical solutions depart from the scope of the technical solutions in the examples of the present disclosure.

The invention claimed is:

1. A *Candida tropicalis* strain Am2525 with the deposition number CCTCC NO: M 2019419.

2. A method of producing a long-chain dicarboxylic acid, comprising: preparing a seed solution comprising a *Candida tropicalis* strain Am2525 with the deposit number CCTCC NO: M 2019419; and fermenting the strain to produce a long-chain dicarboxylic acid.

3. The method according to claim 2, wherein a substrate for fermentation comprises one or more of C10 n-alkanes, C10 straight-chain saturated fatty acids, C10 straight-chain saturated fatty acid esters and C10 straight-chain saturated fatty acid salts.

4. The method according to claim 2, wherein the fermentation step comprises culturing at 28° C. to 31° C. for 90-200 hours, and/or shaking at a speed of 200-250 rpm.

5. The method according to claim 2, comprising the following steps:
   a) activating the strain;
   b) preparing the seed solution;
   c) inoculating the seed solution into a fermentation medium; and
   d) fermenting to produce a long-chain dicarboxylic acid.

6. The method according to claim 5, wherein in step a), a medium for activating the strain comprises Yeast Peptone Dextrose (YPD) medium, and the YPD medium comprises 2.0% w/v of glucose, 1.0% w/v of yeast extract, 2.0% w/v of peptone, and water.

7. The method according to claim 5, wherein, in step b), the seed solution is prepared by inoculating the *Candida tropicalis* strain Am2525 into a culture medium comprising 10-20 g/L of sucrose, 2-4 g/L of corn steep liquor, 3-8 g/L of yeast extract, 4-12 g/L of potassium dihydrogen phosphate, 0.5-4 g/L of urea, and 0-80 mL/L of one or more substrates selected from the group consisting of C10 n-alkanes, C10 straight-chain saturated fatty acids, C10 straight-chain saturated fatty acid esters and C10 straight-chain saturated fatty acid salts.

8. The method according to claim 5, wherein, in step c), the seed solution is inoculated into the fermentation medium in an inoculation amount of 10%-30% by volume.

9. The method according to claim 3, comprising the following steps:
   a) activating the strain;
   b) preparing the seed solution;
   c) inoculating the seed solution into a fermentation medium; and
   d) fermenting to produce a long-chain dicarboxylic acid.

10. The method according to claim 4, comprising the following steps:
    a) activating the strain;
    b) preparing the seed solution;
    c) inoculating the seed solution into a fermentation medium; and
    d) fermenting to produce a long-chain dicarboxylic acid.

11. The method according to claim 2, wherein the long-chain dicarboxylic acid is a C10 straight-chain saturated dicarboxylic acid.

12. The method according to claim 3, wherein the substrate for fermentation is added in an amount of 100-400 mL/L.

\* \* \* \* \*